United States Patent [19]

Matsui et al.

[11] Patent Number: 5,532,387

[45] Date of Patent: Jul. 2, 1996

[54] PROCESS FOR THE PREPARATION OF α-TOCOPHEROL DERIVATIVES

[75] Inventors: Makoto Matsui; Hisashi Yamamoto, both of Aichi Prefecture, Japan

[73] Assignee: Eisai Co., Ltd., Tokyo, Japan

[21] Appl. No.: 352,519

[22] Filed: Dec. 9, 1994

[30] Foreign Application Priority Data

Dec. 14, 1993 [JP] Japan .................................. 5-342074
Oct. 31, 1994 [JP] Japan .................................. 6-267288

[51] Int. Cl.$^6$ .................................................. C07D 311/72
[52] U.S. Cl. ................................................................ 549/411
[58] Field of Search .................................................. 549/411

*Primary Examiner*—Nicky Chan
*Attorney, Agent, or Firm*—Wenderoth, Lind & Ponack

[57] ABSTRACT

A process is provided for the preparation of an α-tocopherol derivative represented by the following formula (VII):

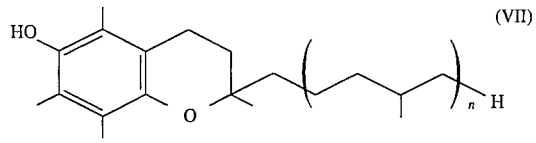

wherein n stands for 0 or an integer of from 1 to 5. According to the process, trimethylhydroquinone and a particular allyl alcohol derivative or a specific alkenyl alcohol are subjected to a condensation reaction in the presence of a fluorosulfonate [M(RSO$_3$)$_3$], a nitrate [M(NO$_3$)$_3$] or a sulfate [M$_2$(SO$_4$)$_3$], wherein M represents a scandium, yttrium or lanthanide atom, and R represents a fluorine atom, a fluorinated lower alkyl group, or an aryl group which may be substituted by one or more fluorine atoms. The lanthanide atom means a lanthanum, cerium, praseodymium, neodymium, promethium, samarium, europium, gadolinium, terbium, dysprosium, holmium, erbium, thulium, ytterbium or lutetium atom.

7 Claims, No Drawings

PROCESS FOR THE PREPARATION OF α-TOCOPHEROL DERIVATIVES

BACKGROUND OF THE INVENTION a) Field of the Invention

This invention relates to a process for the preparation of α-tocopherol derivatives which are useful as antisterile vitamins, hyperlipidemics, blood flow increasing agents, oxygen radical scavengers, anti-cytosenility agents, antioxidants and the like.

b) Description of the Related Art

α-Tocopherol derivatives represented by the following formula (VII):

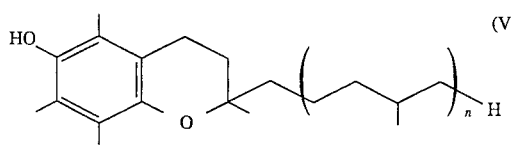
(VII)

wherein n stands for 0 or an integer of from 1 to 5 have heretofore each been prepared by condensing trimethylhydroquinone represented by the following formula (I):

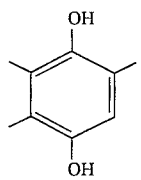
(I)

with one of the phytols represented by the following formulas:

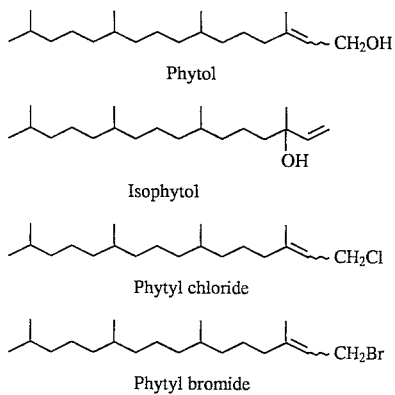

in accordance with a Friedel-Crafts reaction.

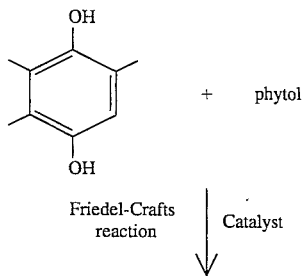

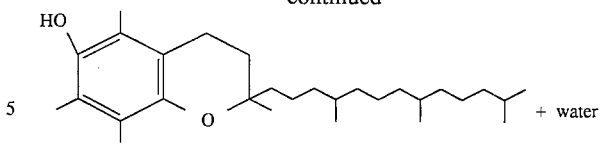
+ water

The catalyst is essential for the Friedel-Crafts reaction. Described specifically, Lewis acids such as zinc chloride, aluminum chloride, stannic chloride, ferric chloride, titanium tetrachloride and boron trifluoride-ether complex as well as combinations of Lewis acids and protonic acids such as hydrochloric acid, sulfuric acid and phosphoric acid have been used. For example, a process employing zinc chloride and a hydrogen halide is disclosed in Japanese Patent Publication No. 21835/70, a process using ferric chloride and hydrogen chloride is disclosed in Japanese Patent Application Laid-open (KOKAI) No. 14176/72; a process employing stannic chloride and hydrogen chloride is disclosed in Japanese Patent Publication No. 21712/70, and a process relying upon a boron trifluoride-ether complex is disclosed in Japanese Patent Publication No. 8821/72.

The catalysts employed in the conventional preparation processes of α-tocopherol derivatives (VII) are accompanied by the problem that they cannot be recovered and reused because they are extremely unstable to water and are decomposed or deactivated upon contact with water formed in the reactions or during washing with water. These catalysts are also accompanied by the economical drawback that they have to be used in a stoichiometrically equivalent amount relative to trimethylhydroquinone or the corresponding phytol and they account for a large percentage of the production cost despite their use as catalysts. They also involve the problem that they require a larger reactor and the disposal of greater waste. Further, it is difficult from the standpoint of environmental conservation to dispose of zinc, tin, phosphorus and the like. The conventional preparation processes are therefore not considered to be industrially suited.

The conventional catalysts employed in the preparation of the α-tocopherol derivatives (VII) involve many problems in economy, handling, waste disposal and the like as described above. It has therefore been desired to develop an industrially excellent catalyst as a substitute for such conventional catalysts.

SUMMARY OF THE INVENTION

An object of the present invention is therefore to provide an industrially excellent process for the preparation of the α-tocopherol derivatives (VII) which are useful as antisterilitic vitamins, blood lipid lowering agents, hyperkinemics, active oxygen eliminating agents, catabiosis preventatives, antioxidants and the like.

The present inventors have therefore proceeded with extensive research to improve the above-described problems of the conventional catalysts. As a result, it has been found that use of a particular fluorosulfonate, nitrate or sulfate can achieve the above object and industrial preparation of the α-tocopherol derivatives (VII).

In one aspect of the present invention, there is thus provided a process for the preparation of an α-tocopherol derivative represented by the following formula (VII):

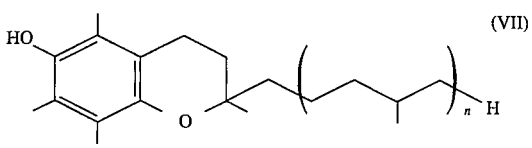
(VII)

wherein n stands for 0 or an integer of from 1 to 5, which comprises subjecting trimethylhydroquinone represented by the following formula (I):

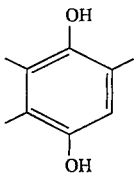
(I)

and an allyl alcohol derivative represented by the following formula (II):

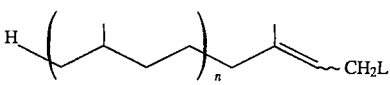
(II)

wherein n has the same meaning as defined above and L represents a hydroxyl group, a halogen atom, acetoxy, methanesulfonyloxy, ethanesulfonyloxy, benzenesulfonyloxy or toluenesulfonyloxy group; or an alkenyl alcohol represented by the following formula (III):

(III)

wherein n has the same meaning as defined above to a condensation reaction in the presence of a fluorosulfonate represented by the following formula (IV):

M(RSO₃)₃ (IV)

wherein M represents a scandium, yttrium or lanthanide atom, R represents a fluorine atom, a fluorinated lower alkyl group, or an aryl group which may be substituted by one or more fluorine atoms, and the lanthanide atom means a lanthanum, cerium, praseodymium, neodymium, promethium, samarium, europium, gadolinium, terbium, dysprosium, holmium, erbium, thulium, ytterbium or lutetium atom; a nitrate represented by the following formula (V):

M (NO₃)₃ (V)

wherein M has the same meaning as defined above; or a sulfate represented by the following formula (VI):

M₂ (SO₄)₃ (VI)

wherein M has the same meaning as defined above.

The fluorosulfonate (IV) or the nitrate (V) employed as a catalyst in the present invention moves to a water layer when washed with water after the reaction. It should be noted that the catalyst is not decomposed or deactivated, unlike Lewis acids in the conventional processes, and hence, the catalyst can be reused by concentrating the water layer. The catalyst is therefore excellent from the industrial standpoint.

DETAILED DESCRIPTION OF THE INVENTION AND PREFERRED EMBODIMENTS

In the allyl alcohol derivative represented by the formula (II), specific examples of the halogen atom include chlorine, bromine, iodine and fluorine atoms. Examples of the allyl alcohol derivative (II) include, but are not limited to, the below-described compounds. Some of these compounds include those containing an asymmetric carbon atom in their molecules. Needless to say, all optically active substances thereof should be included, as well as their racemic mixtures.

(1) Isoprenyl alcohol [also called "3-methyl-2-buten-1-ol"]
(2) Isoprenyl chloride [also called "1-chloro-3 -methyl-2-butene]
(3) Isoprenyl bromide [also called "1-bromo-3 -methyl-2-butene]
(4) Isoprenyl iodide [also called "1-iodo-3 -methyl-2-butene]
(5) 3,7-Dimethyl-2-octen-1-ol
(6) 1-Chloro-3,7-dimethyl-2-octene
(7) 1-Bromo-3,7-dimethyl-2-octene
(8) 1-Iodo-3,7-dimethyl-2-octene
(9) 3,7,11-Trimethyl-2-dodecen-1-ol
(10) 1-Chloro-3,7,11-trimethyl-2-dodecene
(11) 1-Bromo-3,7,11-trimethyl-2-dodecene
(12) 1-Iodo-3,7,11-trimethyl-2-dodecene
(13) Phytol
(14) Phytyl chloride
(15) Phytyl bromide
(16) Phytyl iodide
(17) Phytyl acetate
(18) Phytyl methanesulfonate
(19) Phytyl toluenesulfonate
(20) 3,7,11,15,19-Pentamethyl-2-icosen-1-ol
(21) 1-Chloro-3,7,11,15,19-pentamethyl-2-icosene
(22) 1-Bromo-3,7,11,15,19-pentamethyl-2-icosene
(23) 1-Iodo-3,7,11,15,19-pentamethyl-2-icosene
(24) 3,7,11,15,19,23-Hexamethyl-2-tetracosen-1-ol
(25) 1-Chloro-3,7,11,15,19,23-hexamethyl-2 -tetracosene
(26) 1-Bromo-3,7,11,15,19,23-hexamethyl-2 -tetracosene
(27) 1-Iodo-3,7,11,15,19,23-hexamethyl-2 -tetracosene Next, specific examples of the alkenyl alcohol represented by the formula (III) include, but are not limited to, the below-described compounds. Some of these compounds include those containing an asymmetric carbon atom in their molecules. Needless to say, all optically active substances thereof should be included, as well as their racemic mixtures.

(1) 2-Methyl-3-buten-2-ol
(2) 3,7-Dimethyl-1-octen-3-ol
(3) 3,7,11-Trimethyl-1-dodecen-3-ol
(4) Isophytol
(5) 3,7,11,15,19-Pentamethyl-1-icosen-3-ol
(6) 3,7,11,15,19,23-Hexamethyl-1-tetracosen-3-ol In the fluorosulfonate represented by the formula (IV), the term "lantanide atom" means a lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) or lutetium (Lu) atom. The term "fluorinated lower alkyl group", on the other hand, means a $C_{1-6}$ alkyl group in which one or more hydrogen atoms have been substituted by a corresponding number of fluorine atoms. Specific examples of the fluorinated lower alkyl group include fluoromethyl, difluoromethyl, trifluoromethyl, 1-fluoroethyl, 2-fluoroethyl, 1,1-difluoroethyl, 1,2-difluoroethyl, 2,2-difluoroethyl, 1,1,1-trifluoroethyl, 1,1,2-trifluoroethyl, 1,2,2-trifluoroethyl, 2,2,2-trifluoroethyl, 1,1,1-trifluoropropyl, 1,1,1-trifluorobutyl, 1,1,1-trifluoropentyl and 1,1,1-triflurohexyl groups. The term "aryl group which may be substituted by one or more fluorine atoms" means aryl groups such as phenyl, tolyl ($CH_3C_6H_4$—) and xylyl [($CH_3)_2C_6H_3$—] groups and those obtained by substituting such aryl groups by one or more fluorine atoms. Specific examples include phenyl, tolyl, xylyl, fluorophenyl, difluorophenyl, trifluorophenyl, tetrafluorophenyl, pentafluorophenyl, fluorotolyl, difluorotolyl, trifluorotolyl, tetrafluorotolyl, fluoroxylyl, difluoroxylyl and trifluoroxylyl groups.

The following are specific examples of the fluorosulfonate (IV), but are not limited to:
scandium fluorosulfonate [$Sc(FSO_3)_3$],
yttrium fluorosulfonate [$Y(FSO_3)_3$],
lanthanum fluorosulfonate [$La(FSO_3)_3$],
cerium fluorosulfonate [$Ce(FSO_3)_3$],
praseodymium fluorosulfonate [$Pr(FSO_3)_3$],
neodymium fluorosulfonate [$Nd(FSO_3)_3$],
promethium fluorosulfonate [$Pm(FSO_3)_3$],
samarium fluorosulfonate [$Sm(FSO_3)_3$],
europium fluorosulfonate [$Eu(FSO_3)_3$],
gadolinium fluorosulfonate [$Gd(FSO_3)_3$],
terbium fluorosulfonate [$Tb(FSO_3)_3$],
dysprosium fluorosulfonate [$Dy(FSO_3)_3$],
holmium fluorosulfonate [$Ho(FSO_3)_3$],
erbium fluorosulfonate [$Er(FSO_3)_3$],
thulium fluorosulfonate [$Tm(FSO_3)_3$],
ytterbium fluorosulfonate [$Yb(FSO_3)_3$],
lutetium fluorosulfonate [$Lu(FSO_3)_3$],
scandium trifluoromethanesulfonate [$Sc(CF_3SO_3)_3$],
yttrium trifluoromethanesulfonate [$Y(CF_3SO_3)_3$],
lanthanum trifluoromethanesulfonate [$La(CF_3SO_3)_3$],
    cerium trifluoromethanesulfonate [$Ce(CF_3SO_3)_3$],
praseodymium trifluoromethanesulfonate [$Pr(CF_3SO_3)_3$],
neodymium trifluoromethanesulfonate [$Nd(CF_3SO_3)_3$],
promethium trifluoromethanesulfonate [$Pm(CF_3SO_3)_3$],
samarium trifluoromethanesulfonate [$Sm(CF_3SO_3)_3$],
europium trifluoromethanesulfonate [$Eu(CF_3SO_3)_3$],
gadolinium trifluoromethanesulfonate [$Gd(CF_3SO_3)_3$],
terbium trifluoromethanesulfonate [$Tb(CF_3SO_3)_3$],
dysprosium trifluoromethanesulfonate [$Dy(CF_3SO_3)_3$],
holmium trifluoromethanesulfonate [$Ho(CF_3SO_3)_3$],
erbium trifluoromethanesulfonate [$Er(CF_3SO_3)_3$],
thulium trifluoromethanesulfonate [$Tm(CF_3SO_3)_3$],
ytterbium trifluoromethanesulfonate [$Yb(CF_3SO_3)_3$],
lutetium trifluoromethanesulfonate [$Lu(CF_3SO_3)_3$],
scandium fluorobenzenesulfonate [$Sc\{(FC_6H_4)SO_3\}_3$],
yttrium fluorobenzenesulfonate [$Y\{(FC_6H_4)SO_3\}_3$],
lanthanum fluorobenzenesulfonate [$La\{(FC_6H_4)SO_3\}_3$],
cerium fluorobenzenesulfonate [$Ce\{(FC_6H_4)SO_3\}_3$],
praseodymium fluorobenzenesulfonate [$Pr\{(FC_6H_4)SO_3\}_3$],
neodymium fluorobenzenesulfonate [$Nd\{(FC_6H_4)SO_3\}_3$],
promethium fluorobenzenesulfonate [$Pm\{(FC_6H_4)SO_3\}_3$],
samarium fluorobenzenesulfonate [$Sm\{(FC_6H_4)SO_3\}_3$],
europium fluorobenzenesulfonate [$Eu\{(FC_6H_4)SO_3\}_3$],
gadolinium fluorobenzenesulfonate [$Gd\{(FC_6H_4)SO_3\}_3$],
terbium fluorobenzenesulfonate [$Tb\{(FC_6H_4)SO_3\}_3$],
dysprosium fluorobenzenesulfonate [$Dy\{(FC_6H_4)SO_3\}_3$],
holmium fluorobenzenesulfonate [$Ho\{(FC_6H_4)SO_3\}_3$],
erbium fluorobenzenesulfonate [ $Er\{(FC_6H_4)SO_3\}_3$],
thulium fluorobenzenesulfonate [$Tm\{(FC_6H_4)SO_3\}_3$],
ytterbium fluorobenzenesulfonate [$Yb\{(FC_6H_4)SO_3\}_3$], and
lutetium fluorobenzenesulfonate [$Lu\{(FC_6H_4)SO_3\}_3$].

Each fluorosulfonate (IV) useful in the practice of the present invention can be prepared from scandium oxide, yttrium oxide or a lanthanide oxide and fluorosulfonic acid, trifluoromethanesulfonic acid or the like in accordance with the process disclosed in U.S. Pat. No. 3,615,169, Journal of Organic Chemistry (J. Org. Chem.), 52(6), 1017 (1987) or the like.

Further, specific examples of the nitrate represented by the formula (V) include, but are not limited to, scandium nitrate [$Sc(NO_3)_3$], yttrium nitrate [$Y(NO_3)_3$], lanthanum nitrate [$La(NO_3)_3$], cerium nitrate [$Ce(NO_3)_3$], praseodymium nitrate [$Pr(NO_3)_3$], neodymium nitrate [$Nd(NO_3)_3$], promethium nitrate [$Pr(NO_3)_3$], samarium nitrate [$Sm(NO_3)_3$], europium nitrate [$Eu(NO_3)_3$], gadolinium nitrate [$Gd(NO_3)_3$], terbium nitrate [$Tb(NO_3)_3$], dysprosium nitrate [$Dy(NO_3)_3$], holmium nitrate [$Ho(NO_3)_3$], erbium nitrate [$Er(NO_3)_3$], thulium nitrate [$Tm(NO_3)_3$], ytterbium nitrate [$Yb(NO_3)_3$] and lutetium nitrate [$Lu(NO_3)_3$].

Each nitrate (V) useful in the practice of the present invention is readily available as a reagent or an industrial material.

Specific examples of the sulfate (VI) include, but are not limited to, scandium sulfate [$Sc2(SO4)3$], yttrium sulfate [$Y_2(SO_4)_3$], lanthanum sulfate [$La_2(SO_4)_3$], cerium sulfate [$Ce_2(SO_4)_3$], praseodymium sulfate [$Pr_2(SO_4)_3$], neodymium sulfate [$Nd_2(SO_4)_3$], promethium sulfate [$Pr_2(SO_4)_3$], samarium sulfate [$Sm_2(SO_4)_3$], europium sulfate [$Eu_2(SO_4)_3$], gadolinium sulfate [$Gd_2(SO_4)_3$], terbium sulfate [$Tb_2(SO_4)_3$], dysprosium sulfate [$Dy_2(SO_4)_3$], holmium sulfate [$Ho_2(SO_4)_3$], erbium sulfate [$Er_2(SO_4)_3$], thulium sulfate [$Tin_2(SO_4)_3$], ytterbium sulfate [$Yb_2(SO_4)_3$] and lutetium sulfate [$Lu(SO_4)_3$].

Each sulfate (VI) useful in the practice of the present invention is readily available as a reagent or an industrial material.

Finally, specific examples of the α-tocopherol derivative (VII) available according to the present invention include, but are not limited to, the below-described compounds. Some of these compounds include those containing an asymmetric carbon atom in their molecules. Needless to say, all optically active substances thereof should be included, as well as their racemic mixtures.

(1) 3,4-Dihydro-2,5,7,8-tetramethyl-2-methyl-2 H-1- benzopyran-6-ol (2) 3,4-Dihydro-2,5,7,8-tetramethyl-2-(4 -methylpentyl)-2H-1-benzopyran-6-ol (3) 3,4-Dihydro-2,5,7,8-tetramethyl-2-(4,8 -dimethylnonyl)-2H-1-benzopyran-6-ol (4) α-Tocopherol (5) 3,4-Dihydro-2,5,7,8-tetramethyl-2-(4,8,12,16 -tetramethylheptadecyl)-2H-1-benzopyran-6-ol (6) 3,4-Dihydro-2,5,7,8-tetramethyl-2-(4,8,12,16, 20)-pentamethylhenicosyl)-2H-1-benzopyran-6 -ol The preparation process according to the present invention will hereinafter be described in detail.

The preparation process can be conducted in a manner known per se in the art with respect to Friedel-Crafts reactions. In general, however, the trimethylhydroquinone (I) and the catalyst are mixed together and after adding a solvent as needed, the resulting mixture is added with the allyl alcohol derivative (II) or the alkenyl alcohol (III) in an amount of about 0.9–1.1 equivalents relative to the trimethylhydroquinone (I). It is preferred to conduct the reaction under a stream of an inert gas such as nitrogen or argon, although the reaction can be conducted without such an inert gas stream. The present invention is therefore not limited to the use of such an inert gas stream.

Where a solvent is employed, no particular limitation is imposed on the solvent insofar as it is inert to the trimethylhydroquinone (I), the allyl alcohol derivative (II) or the alkenyl alcohol (III), and the catalyst. Specific examples include benzene, toluene, xylene, nitrobezene, chlorobenzene, dichlorobenzene, nitromethane, tetrahydrofuran, 1,2-dimethoxyethane, diethyl ether, diisopropyl ether, dibutyl ether, methyl acetate, ethyl acetate, propyl acetate, methyl propionate, ethyl propionate, methyl butyrate, ethyl butyrate, hexane, octane, decane, decalin, methylene chloride, chloroform, carbon tetrachloride, 1,2-dichloroethane, 1,1,1-trichloroethane, 1,1,2-trichloroethane, Tri-clene, 1,1,1,2-tetrachloroethane, 1,1,2,2,-tetrachloroethane, 1-chloropropane, 2-chloropropane, 1,1-dichloropropane, 1,2-dichloropropane, 1,3-dichloropropane, 2,2-dichloropropane, 1,4-dioxane, and 1,3-dioxolane. Preferred are benzene, toluene, xylene, nitrobenzene, chlorobenzene, nitromethane, ethyl acetate, propyl acetate, methyl propionate, ethyl propionate, methyl butyrate, ethyl butyrate, methylene chloride, 1,2-dichloroethane, 1,1,1-trichloroethane, 1,1,2-trichloroethane and Tri-clene, with benzene, toluene, xylene, nitrobenzene, nitromethane, ethyl acetate and methylene chloride being more preferred.

Although no particular limitation is imposed on the amount of the solvent to be used, the solvent may be employed usually in an amount of about 0.5–100 volumes, preferably in an amount of about 0.7–50 volumes, and more preferably in an amount of about 1–20 volumes, all relative to the trimethylhydroquinone (I). Incidentally, the above-exemplified solvents can be used either singly or in combination.

No particular limitation is imposed on the amount of the catalyst to be used in the present invention. The catalyst may be employed usually in an amount of about 0.0001–1.5 equivalents, preferably in an amount of about 0.0005–1.0 equivalent, and more preferably in an amount of about 0.001–0.5 equivalent, all relative to the trimethylhydroquinone (I). As is appreciated from this, it is not necessary for the process of the present invention to use the catalyst stoichiometrically as in the conventional processes.

In the present invention, the reaction can be conducted at room temperature to the reflux temperature of the solvent. Heating under reflux is generally preferred to shorten the reaction time. When heated under reflux, the reaction is generally completed in 1–12 hours or so. The reaction time can be shortened further by azeotropically removing water.

The α-tocopherol derivative (VII) so prepared can be purified by a method known per se in the art, such as chromatography on a silica gel column, HPLC or molecular distillation.

The fluorosulfonate (IV), the nitrate (V) or the sulfate (VI) employed as a catalyst in the present invention moves to a water layer when washed with water after the reaction. As the catalyst is not decomposed or deactivated, unlike Lewis acids in the conventional processes, the catalyst can be reused by concentrating the water layer. The catalyst is therefore excellent from the industrial standpoint.

To specifically describe the present invention, Examples will be set forth hereinafter. Needless to say, it should be borne in mind that the present invention is not limited to the Examples.

EXAMPLE 1

(Synthesis of α-Tocopherol)

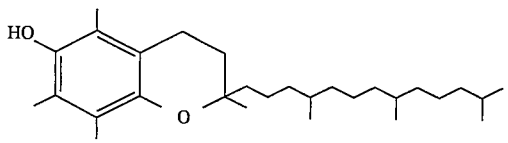

Suspended in 20 ml of ethyl acetate were 10.0 g (65.8 mmol) of trimethylhydroquinone (TMH) and 0.32 g (0.658 mmol) of scandium trifluoromethanesulfonate, followed by heating under reflux for 10 minutes under an argon gas stream. After a solution of 20.3 g (68.4 mmol) of isophytol in 20 ml of ethyl acetate was added dropwise over 30 minutes under heating and reflux, TMH and isophytol were reacted for 3 hours. The reaction mixture was cooled, to which 100 ml of toluene were added. The resulting mixture was washed twice with 200-ml portions of water and then concentrated under reduced pressure. The residue was added with 100 ml of toluene and 100 ml of 2-butanone. The organic layer was washed twice with 200-ml portions of a 1N aqueous solution of sodium hydroxide and then with 200 ml of a saturated aqueous solution of sodium chloride. The organic layer was then dried over magnesium sulfate and concentrated under reduced pressure. The residue was purified by chromatography on a silica gel column (eluent: n-hexane-diethyl ether system), whereby 28.1 g of the title compound were obtained in the form of a brown oil. (Yield: 99%, GLC purity: 95%)

The product was identified with a standard sample in TLC, HPLC, capillary GLC, $^1$H-NMR spectrum, IR spectrum and mass spectrum.

EXAMPLES 2–7

(Synthesis of α-Tocopherol)

The procedures of Example 1 were repeated in a similar manner except that certain reaction conditions were changed as shown in Table 1. The results are shown in Table 1.

TABLE 1

| Example | Amount Of catalyst* | Solvent | Reaction conditions | Yield | Purity** |
|---|---|---|---|---|---|
| 2 | 0.2 | Xylene | Heated under reflux, 3 hrs | 88% | 97% |
| 3 | 0.2 | Toluene | Heated under reflux, 6 hrs | 98% | 98% |
| 4 | 0.01 | Toluene | Heated under reflux, 3 hrs | 86% | 92% |
| 5 | 0.001 | Toluene | Azeotropic dehydration, 3 hrs | 79% | 96% |
| 6 | 0.2 | Benzene | Heated under reflux, 6 hrs | 98% | 96% |
| 7 | 0.001 | Ethyl acetate | Azeotropic dehydration, 3 hrs | 90% | 95% |

*Amount of catalyst: Number of equivalent of scandium methanesulfonate relative to TMH.
**Purity: GLC purity

EXAMPLE 8

(Synthesis of α-Tocopherol)

Suspended in 200 me of xylene were 20.0 g (131.6 mmol) of TMH and 15.8 g (26.3 mmol) of europium trifluoromethanesulfonate, followed by heating under reflux for 5 minutes under an argon gas stream. After a solution of 43.0 g (145.0 mmol) of isophytol in 200 ml of methylene chloride was added dropwise over 30 minutes under heating and reflux, TMH and isophytol were reacted for 3 hours. The reaction mixture was cooled, to which 1,000 ml of ethyl acetate were added. The resulting mixture was washed thrice with 2,000-ml portions of water and then with 2,000 ml of a saturated aqueous solution of sodium chloride. The organic layer was then dried over magnesium sulfate and concentrated under reduced pressure. The residue was purified by chromatography on a silica gel column (eluent: n-hexane-diethyl ether system), whereby 47.7 g of the title compound were obtained in the form of a brown oil. (Yield: 84%, GLC purity: 80%)

EXAMPLE 9

(Synthesis of α-Tocopherol)

Suspended in 100 ml of xylene were 20.0 g (131.6 mmol) of TMH and 16.3 g (26.3 mmol) of ytterbium trifluoromethanesulfonate, followed by heating under reflux for 5 minutes under an argon gas stream. After a solution of 43.0 g (145.0 mmol) of isophytol in 100 ml of xylene was added dropwise over 30 minutes under heating and reflux, TMH and isophytol were reacted for 3 hours. The reaction mixture was cooled, to which 1,000 ml of ethyl acetate were added. The resulting mixture was washed thrice with 2,000-ml portions of water and then with 2,000 ml of a saturated aqueous solution of sodium chloride. The organic layer was then dried over magnesium sulfate and concentrated under reduced pressure. The residue was purified by chromatography on a silica gel column (eluent: n-hexane-diethyl ether system), whereby 35.5 g of the title compound were obtained in the form of a brown oil. (Yield: 59%, GLC purity: 91%)

EXAMPLE 10

(Synthesis of α-Tocopherol)

Suspended in 200 ml of nitromethane were 20.0 g (131.6 mmol) of TMH and 14.1 g (26.3 mmol) of yttrium trifluoromethanesulfonate, followed by heating under reflux for 5 minutes under an argon gas stream. After a solution of 43.0 g (145.0 mmol) of isophytol in 100 ml of diethyl ether was added dropwise over 30 minutes under heating and reflux, TMH and isophytol were reacted for 3 hours. The reaction mixture was cooled, to which 1,000 ml of ethyl acetate were added. The resulting mixture was washed thrice with 2,000-ml portions of water and then with 2,000 ml of a saturated aqueous solution of sodium chloride. The organic layer was then dried over magnesium sulfate and concentrated under reduced pressure. The residue was purified by chromatography on a silica gel column (eluent: n-hexane-diethyl ether system), whereby 46.4 g of the title compound were obtained in the form of a brown oil. (Yield: 82%, GLC purity: 99%)

EXAMPLE 11

(Synthesis of α-Tocopherol)

In a vacuum, 8.0 g (26.3 mmol) of scandium nitrate tetrahydrate were heated and activated. TMH (20.0 g; 131.6 mmol) and 150 ml of toluene were added to scandium nitrate so obtained, whereby scandium nitrate was suspended. The resulting suspension was heated under reflux for 5 minutes under an argon gas stream. After a solution of 43.0 g (145.0 mmol) of isophytol in 50 ml of toluene was added dropwise over 30 minutes under heating and reflux, TMH and isophytol were reacted for 3 hours. The reaction mixture was cooled, to which 1,000 ml of ethyl acetate were added. The resulting mixture was washed thrice with 2,000-ml portions of water and then with 2,000 ml of a saturated aqueous solution of sodium chloride. The organic layer was then dried over magnesium sulfate and concentrated under reduced pressure. The residue was purified by chromatography on a silica gel column (eluent: n-hexane-diethyl ether system), whereby 35.1 g of the title compound were obtained in the form of a brown oil. (Yield: 62%, GLC purity: 99%)

EXAMPLE 12

(Synthesis of α-Tocopherol)

Suspended in 200 ml of toluene were 20.0 g (131.6 mmol) of TMH and 4.5 g (13.2 mmol) of scandium fluorosulfonate, followed by heating under reflux for 5 minutes under an argon gas stream. After a solution of 43.0 g (145.0 mmol) of isophytol in 100 ml of toluene was added dropwise over 30 minutes under heating and reflux, TMH and isophytol were reacted for 3 hours. The reaction mixture was cooled, to which 1,000 ml of ethyl acetate were added. The resulting mixture was washed thrice with 2,000-ml portions of water and then with 2,000 ml of a saturated aqueous solution of sodium chloride. The organic layer was then dried over magnesium sulfate and concentrated under reduced pressure. The residue was purified by chromatography on a silica gel column (eluent: n-hexane-diethyl ether system), whereby 55.4 g of the title compound were obtained in the form of a brown oil. (Yield: 98%, GLC purity: 81%).

EXAMPLE 13

(Synthesis of α-Tocopherol) (Reuse of catalyst)

Suspended in 2 ml of toluene were 1.0 g (6.58 mmol) of TMH and 0.032 g (0.0658 mmol) of scandium trifluoromethanesulfonate, followed by heating under reflux for 10 minutes under an argon gas stream. After a solution of 2.03 g (6.82 mmol) of isophytol in 2 ml of toluene was added dropwise, over 30 minutes under heating and reflux, to the suspension, the reaction was effected for additional 3 hours. The reaction solution was cooled, to which 10 ml of toluene were added. After the resulting mixture was washed twice with 20-ml portions of water, the organic layer was dried over magnesium sulfate and concentrated under reduced pressure. The residue was purified by chromatography on a silica gel column (eluent: n-hexane-diethyl ether system), whereby 2.759 g of the title compound were obtained in the form of a brown oil. (Yield: 96%, GLC purity: 95%).

The water layers obtained upon washing in the above procedures were combined and concentrated under reduced pressure. The residue was added with toluene, and then subjected to azeotropic dehydration to recover the catalyst.

Suspended in 2 ml of toluene were 1.0 g (6.58 mmol) of TMH and the entire amount of the scandium trifluoromethanesulfonate recovered above, followed by heating under reflux for 10 minutes under an argon gas stream. After a solution of 2.03 g (6.82 mmol) of isophytol in 2ml of toluene was added dropwise, over 30 minutes under heating and reflux, to the suspension, the reaction was effected for additional 3 hours. The reaction solution was cooled, to which 10 ml of toluene were added. After the resulting mixture was washed twice with 20-ml portions of water, the organic layer was dried over magnesium sulfate and concentrated under reduced pressure. The residue was purified by chromatography on a silica gel column (eluent: n-hexane-diethyl ether system), whereby 2.57 g of the title compound were obtained in the form of a brown oil. (Yield: 91%, GLC purity: 94%).

What is claimed is:

1. A process for the preparation of an α-tocopherol derivative represented by the following formula (VII):

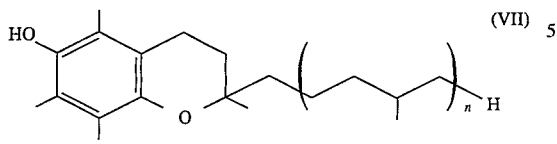

wherein n stands for 0 or an integer of from 1 to 5, which comprises subjecting trimethylhydroquinone represented by the following formula (I):

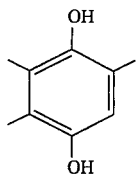

and an allyl alcohol derivative represented by the following formula (II):

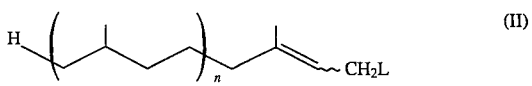

wherein n has the same meaning as defined above and L represents a hydroxyl group, a halogen atom, acetoxy, methanesulfonyloxy, ethanesulfonyloxy, benzenesulfonyloxy or toluenesulfonyloxy group; or an alkenyl alcohol represented by the following formula (III):

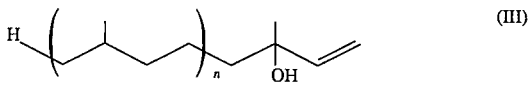

wherein n has the same meaning as defined above to a condensation reaction in the presence of a fluorosulfonate represented by the following formula (IV):

$$M(RSO_3)_3 \quad (IV)$$

wherein M represents a scandium, yttrium or lanthanide atom, R represents a fluorine atom, a fluorinated lower alkyl group, or an aryl group which may be substituted by one or more fluorine atoms, and the lanthanide atom means a lanthanum, cerium, praseodymium, neodymium, promethium, samarium, europium, gadolinium, terbium, dysprosium, holmium, erbium, thulium, ytterbium or lutetium atom; a nitrate represented by the following formula (V):

$$M(NO_3)_3 \quad (V)$$

wherein M has the same meaning as defined above; or a sulfate represented by the following formula (VI):

$$M_2(SO_4)_3 \quad (VI)$$

wherein M has the same meaning as defined above.

2. A process according to claim 1, wherein in the fluorosulfonate (IV), R represents a fluorine atom or a trifluoromethyl, pentafluoroethyl, phenyl, tolyl, xylyl, fluorophenyl, fluorotolyl or fluoroxylyl group.

3. A process according to claim 1, wherein the fluorosulfonate (IV) is at least one fluorosulfonate selected from the group consisting of scandium fluorosulfonate, yttrium fluorosulfonate, lanthanum fluorosulfonate, cerium fluorosulfonate, praseodymium fluorosulfonate, neodymium fluorosulfonate, promethium fluorosulfonate, samarium fluorosulfonate, europium fluorosulfonate, gadolinium fluorosulfonate, terbium fluorosulfonate, dysprosium fluorosulfonate, holmium fluorosulfonate, erbium fluorosulfonate, thulium fluorosulfonate, ytterbium fluorosulfonate, lutetium fluorosulfonate, scandium trifluoromethanesulfonate, yttrium trifluoromethanesulfonate, lanthanum trifluoromethanesulfonate, cerium trifluoromethanesulfonate, praseodymium trifluoromethanesulfonate, neodymium trifluoromethanesulfonate, promethium trifluoromethanesulfonate, samarium trifluoromethanesulfonate, europium trifluoromethanesulfonate, gadolinium trifluoromethanesulfonate, terbium trifluoromethanesulfonate, dysprosium trifluoromethanesulfonate, holmium trifluoromethanesulfonate, erbium trifluoromethanesulfonate, thulium trifluoromethanesulfonate, ytterbium trifluoromethanesulfonate, lutetium trifluoromethanesulfonate, scandium fluorobenzenesulfonate, yttrium fluorobenzenesulfonate, lanthanum fluorobenzenesulfonate, cerium fluorobenzenesulfonate, praseodymium fluorobenzenesulfonate, neodymium fluorobenzenesulfonate, promethium fluorobenzenesulfonate, samarium fluorobenzenesulfonate, europium fluorobenzenesulfonate, gadolinium fluorobenzenesulfonate, terbium fluorobenzenesulfonate, dysprosium fluorobenzenesulfonate, holmium fluorobenzenesulfonate, erbium fluorobenzenesulfonate, thulium fluorobenzenesulfonate, ytterbium fluorobenzenesulfonate, and lutetium fluorobenzenesulfonate.

4. A process according to claim 1, wherein the nitrate (V) is at least one nitrate selected from the group consisting of scandium nitrate, yttrium nitrate, lanthanum nitrate, cerium nitrate, praseodymium nitrate, neodymium nitrate, promethium nitrate, samarium nitrate, europium nitrate, gadolinium nitrate, terbium nitrate, dysprosium nitrate, holmium nitrate, erbium nitrate, thulium nitrate, ytterbium nitrate and lutetium nitrate.

5. A process according to claim 1, wherein the sulfate (VI) is at least one sulfate selected from the group consisting of scandium sulfate, yttrium sulfate, lanthanum sulfate, cerium sulfate, praseodymium sulfate, neodymium sulfate, promethium sulfate, samarium sulfate, europium sulfate, gadolinium sulfate, terbium sulfate, dysprosium sulfate, holmium sulfate, erbium sulfate, thulium sulfate, ytterbium sulfate and lutetium sulfate.

6. A process according to claim 1, wherein at least one compound selected from the group consisting of toluene, xylene, ethyl acetate and nitromethane is used as a solvent.

7. A process according to claim 1, wherein the fluorosulfonate (IV), the nitrate (V) or the sulfate (VI) is used in an amount of 0.0001–1.5 equivalents relative to trimethylhydroquinone (I).

* * * * *